(12) United States Patent
Dorsey

(10) Patent No.: US 10,252,800 B1
(45) Date of Patent: Apr. 9, 2019

(54) AERIAL DRONE DEPLOYED NON-DESTRUCTIVE EVALUATION SCANNER

(71) Applicant: ScanTech Instruments, Inc., Longview, TX (US)

(72) Inventor: Harvey Alan Dorsey, Longview, TX (US)

(73) Assignee: ScanTech Industries, Inc., Longview, TX (US)

( * ) Notice: Subject to any disclaimer, the term of this patent is extended or adjusted under 35 U.S.C. 154(b) by 0 days.

(21) Appl. No.: 16/127,218

(22) Filed: Sep. 10, 2018

Related U.S. Application Data

(63) Continuation-in-part of application No. 15/333,181, filed on Oct. 24, 2016, now Pat. No. 10,072,745.

(60) Provisional application No. 62/725,270, filed on Aug. 31, 2018, provisional application No. 62/245,983, filed on Oct. 23, 2015.

(51) Int. Cl.
*B64D 1/02* (2006.01)
*B66D 1/60* (2006.01)
*B62D 57/024* (2006.01)
*G01N 29/28* (2006.01)
*G01N 29/22* (2006.01)
*B64C 39/02* (2006.01)

(52) U.S. Cl.
CPC ............ *B64D 1/02* (2013.01); *B62D 57/024* (2013.01); *B64C 39/024* (2013.01); *B66D 1/60* (2013.01); *G01N 29/28* (2013.01); *B64C 2201/024* (2013.01); *B64C 2201/12* (2013.01); *G01N 29/225* (2013.01)

(58) Field of Classification Search
CPC .......... B64D 1/02; B66D 1/60; B62D 57/024; B64C 39/024; B64C 2201/12; B64C 2201/024; G01N 29/28; G01N 29/225
See application file for complete search history.

(56) References Cited

U.S. PATENT DOCUMENTS

| | | | | |
|---|---|---|---|---|
| 3,836,841 A | * | 9/1974 | Morrison | G01V 3/165 324/224 |
| 3,872,375 A | * | 3/1975 | Ronka | G01V 3/165 244/1 TD |
| 3,976,937 A | * | 8/1976 | Hearn | G01V 3/165 324/331 |

(Continued)

*Primary Examiner* — Daniel S Larkin
*Assistant Examiner* — Anthony W Megna Fuentes
(74) *Attorney, Agent, or Firm* — Mark W Handley; Handley Law Firm, PLLC

(57) ABSTRACT

A aerial drone deployed NDE scanner test unit (12) has a yoke to which four sets of offset pins (294, 354) pivotally secure a sensor probe (232) in a configuration for rotating about the X-axis and the Y-axis with constrained rotation. Each set of the offset pins (294, 354) are spaced apart, with the ends closest to the terminal ends of the sensor probe (232) and an EUT (26) being more closely spaced than opposite ends of the offset pins (294, 354). The NDE scanner (16) is deployed from an aerial drone (14) with a cable (18) and an umbilical (20) connecting there-between. The cable (18) selectively secures the NDE scanner (16) to the aerial drone (14) and the umbilical (20) provides data and fluid connections. The NDE scanner (16) has a stand-off mechanism (118) which is selectively operated to engage and disengage the magnetic wheels (94) of the NDE scanner (16) from a metal surface of the EUT (26).

17 Claims, 13 Drawing Sheets

(56) References Cited

U.S. PATENT DOCUMENTS

| | | | | |
|---|---|---|---|---|
| 4,628,266 | A * | 12/1986 | Dzwinel | G01V 3/165 |
| | | | | 324/330 |
| 5,331,578 | A * | 7/1994 | Stieler | E21B 47/022 |
| | | | | 33/1 N |
| 7,365,544 | B2 * | 4/2008 | McCracken | G01V 3/16 |
| | | | | 250/253 |
| 8,347,724 | B2 * | 1/2013 | Brignac | G01N 29/07 |
| | | | | 73/618 |
| 10,011,352 | B1 * | 7/2018 | Dahlstrom | B64C 39/022 |
| 10,108,072 | B1 * | 10/2018 | Sugaki | B63B 22/00 |
| 2005/0001622 | A1 * | 1/2005 | Morrison | G01V 3/165 |
| | | | | 324/330 |
| 2008/0211506 | A1 * | 9/2008 | Klinkert | H01Q 1/28 |
| | | | | 324/330 |
| 2011/0115489 | A1 * | 5/2011 | Morrison | B64D 3/00 |
| | | | | 324/330 |
| 2013/0233964 | A1 * | 9/2013 | Woodworth | B64C 37/02 |
| | | | | 244/2 |
| 2014/0263852 | A1 * | 9/2014 | Walker | B64C 39/022 |
| | | | | 244/53 R |
| 2015/0377405 | A1 * | 12/2015 | Down | B64C 39/024 |
| | | | | 73/865.8 |
| 2016/0375984 | A1 * | 12/2016 | Priest | B64C 27/06 |
| | | | | 701/3 |
| 2017/0066530 | A1 * | 3/2017 | Salzmann | B64C 27/04 |
| 2017/0328814 | A1 * | 11/2017 | Castendyk | B64C 39/024 |
| 2018/0072420 | A1 * | 3/2018 | Prager | B64C 39/024 |
| 2018/0232871 | A1 * | 8/2018 | Terry | G06T 7/001 |
| 2018/0244391 | A1 * | 8/2018 | Curran | B64C 39/024 |
| 2018/0244400 | A1 * | 8/2018 | Gamble | B64F 1/02 |
| 2018/0312247 | A1 * | 11/2018 | Ichihara | B64C 27/08 |
| 2018/0327093 | A1 * | 11/2018 | von Flotow | B64D 5/00 |

* cited by examiner

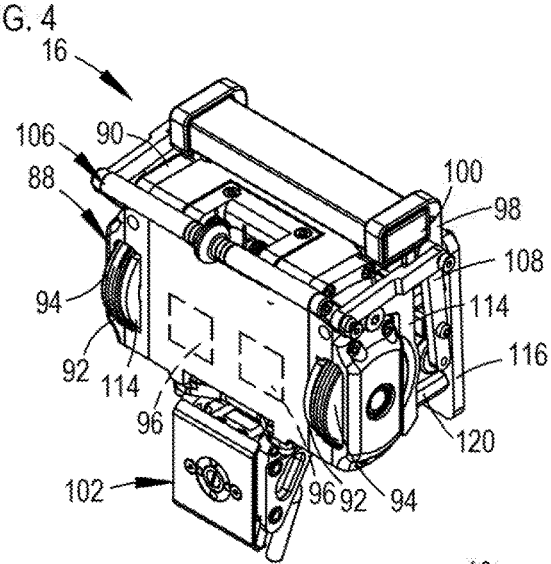
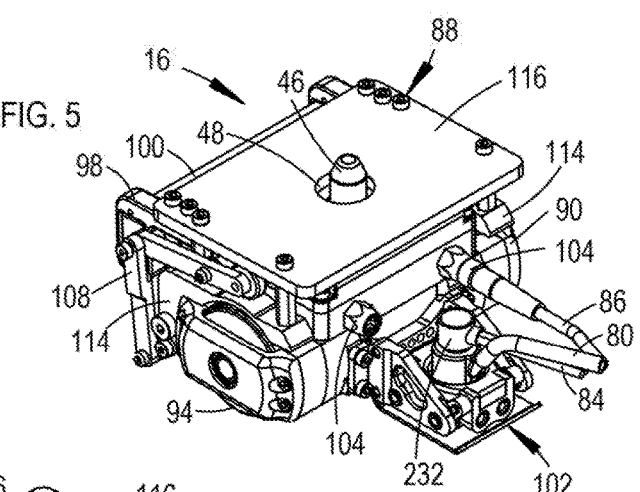
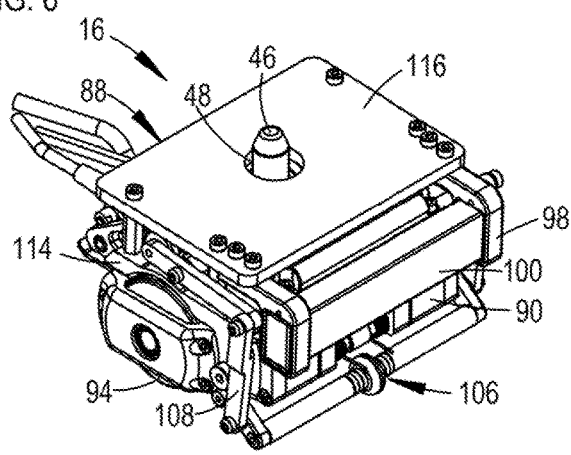

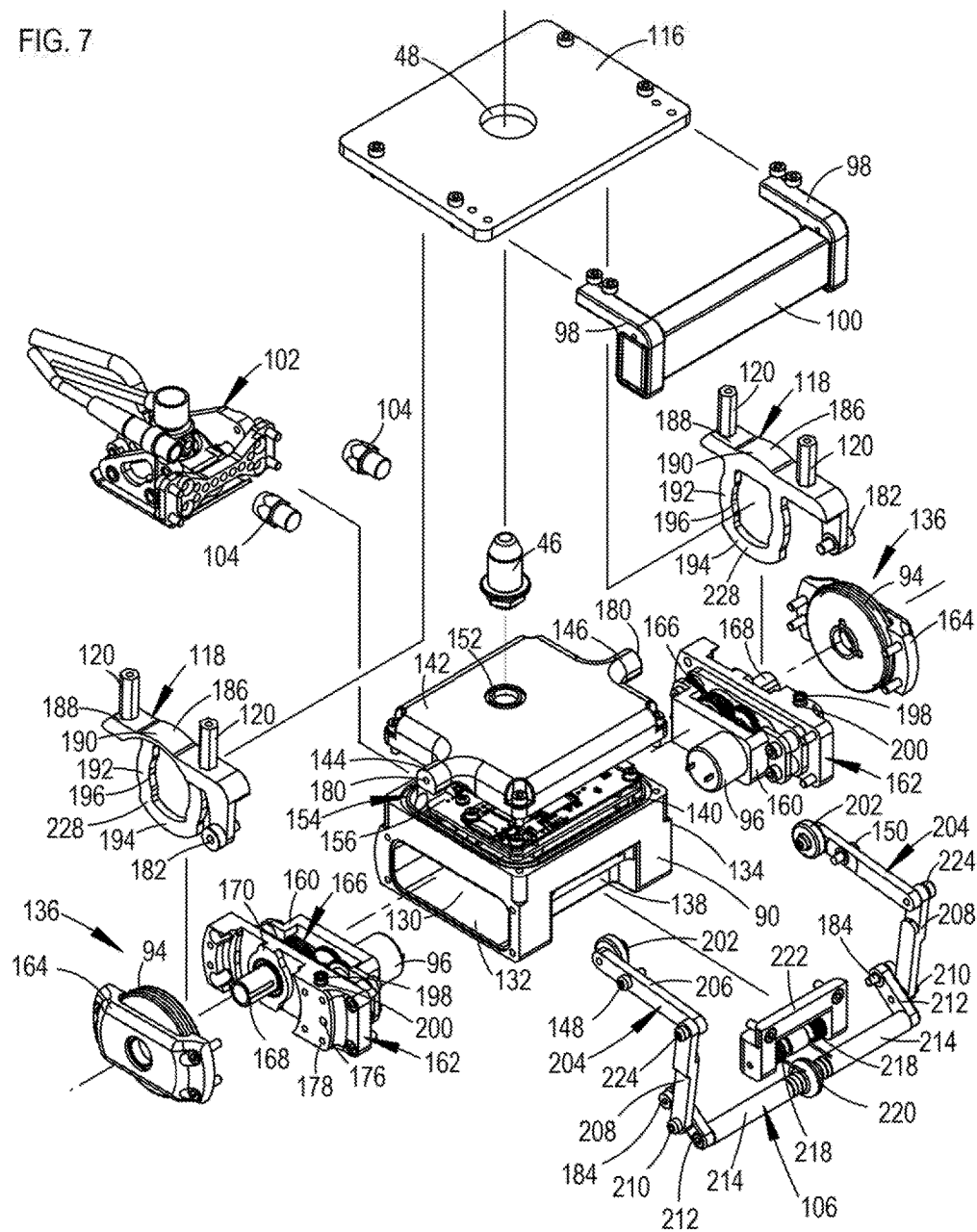

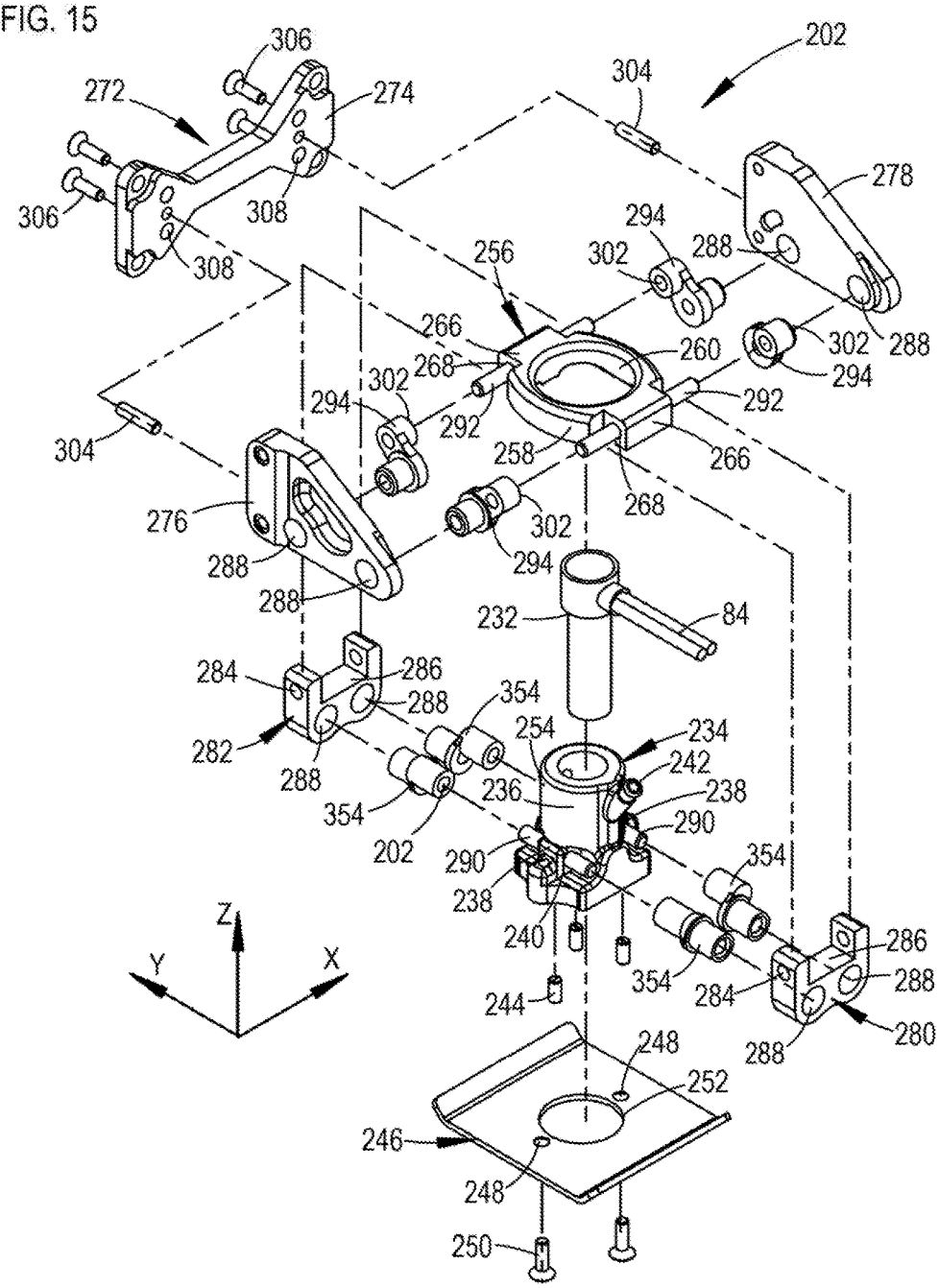

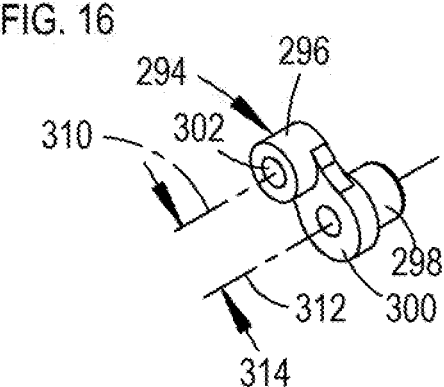
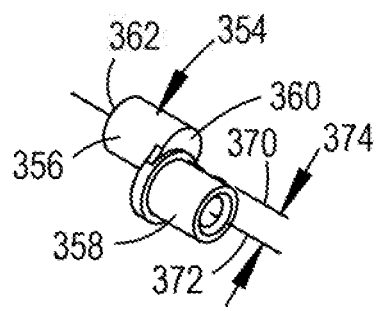
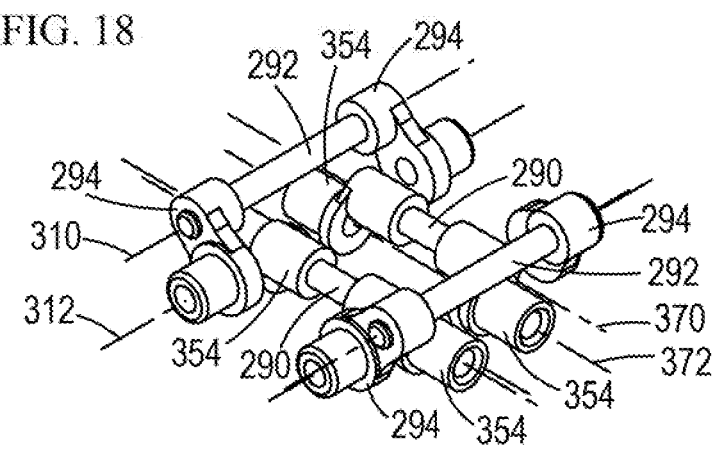
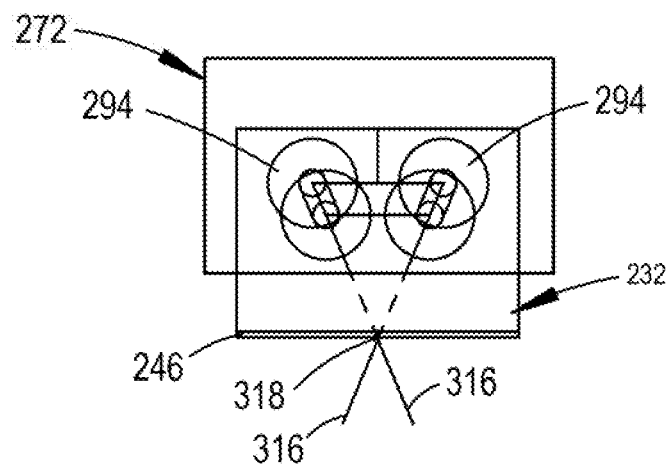

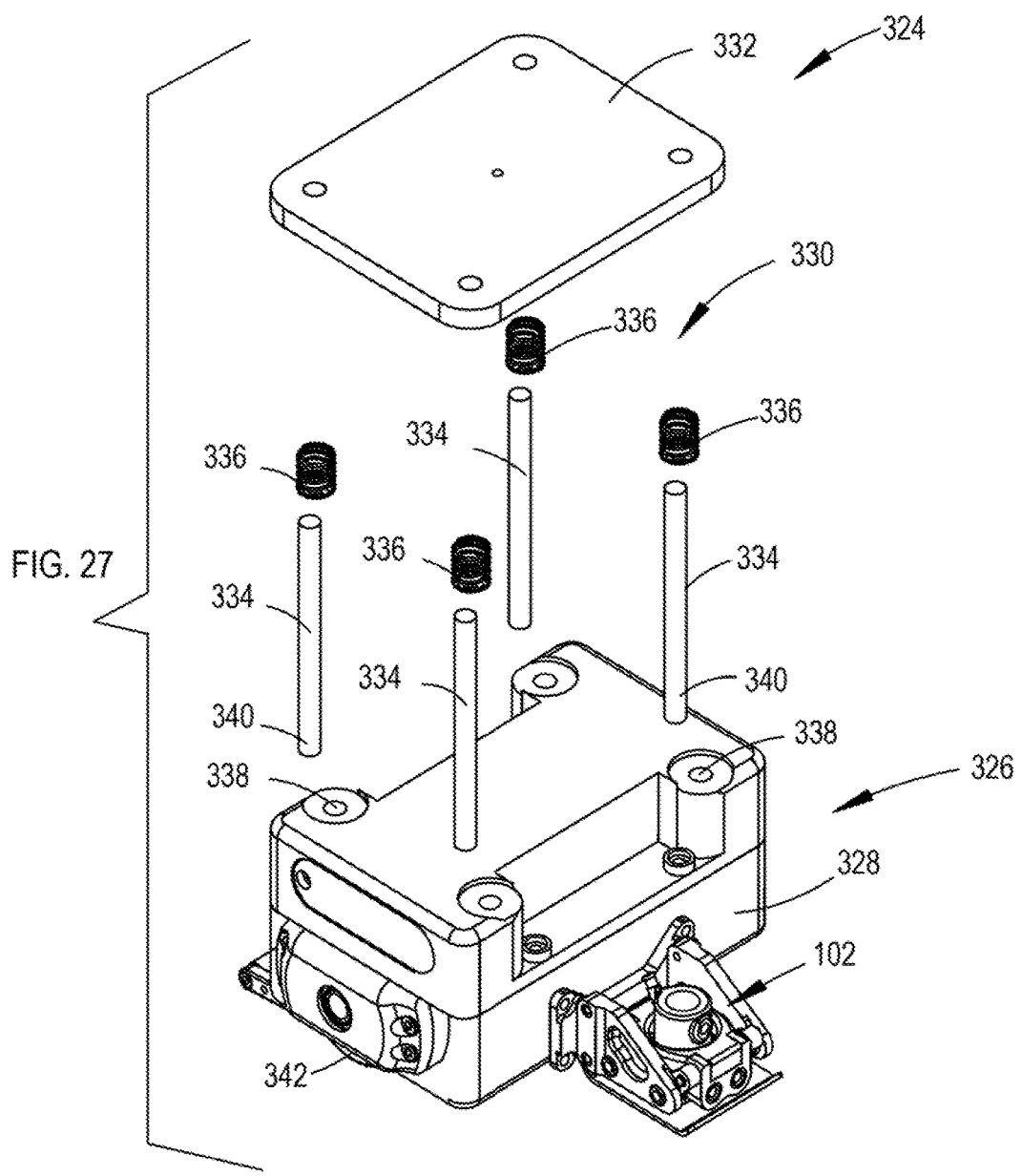

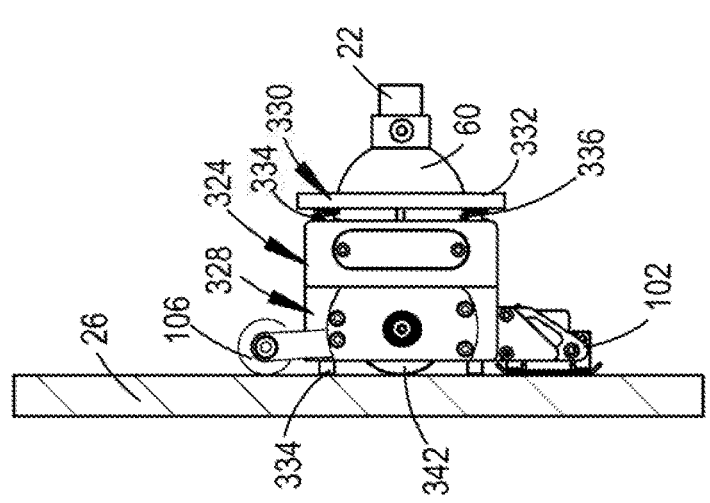
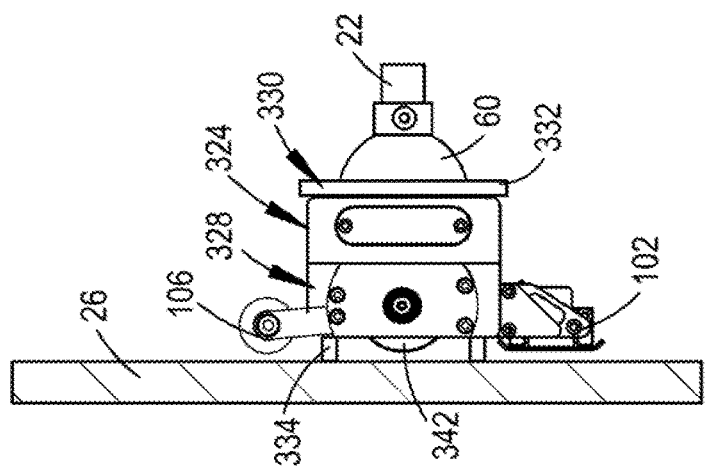

AERIAL DRONE DEPLOYED NON-DESTRUCTIVE EVALUATION SCANNER

CROSS-REFERENCE TO RELATED APPLICATION

The present application is a continuation-in-part of U.S. Provisional Patent Application No. 62/725,270, filed Aug. 31, 2018, and invented by Harvey Alan Dorsey, and a continuation-in-part of U.S. Pat. No. 10,072,724, issued Sep. 11, 2018, having application Ser. No. 15/333,181, filed Oct. 24, 2016, and invented by Harvey Alan Dorsey, which is a conversion to a regular utility application of U.S. Provisional Patent Application Ser. No. 62/245,983, filed Oct. 23, 2015, and invented by Harvey Alan Dorsey.

TECHNICAL FIELD OF THE INVENTION

The present invention relates in general to devices for deploying and transporting non-destructive inspection scanners across surfaces of equipment under inspection, and in particular to a combination of an aerial drone and NDE scanner for field deployment.

BACKGROUND OF THE INVENTION

Non-Destructive Evaluation scanners ("NDE scanners") are commonly used for inspecting Equipment Under Test ("EUT") such as fuel tanks and chemical storage tanks in field industrial applications. NDE scanners typically have sensor probes which include ultrasonic transducers, electromagnetic transducers, or optical transducers, which emit measurement signals and receive return signals in response thereto. The emitted measurement signals are affected by the material of the EUT being inspected to provide the return signals which are representative of the physical conditions of the EUT.

Probes are typically mounted in floating platforms which will remain in fixed orientation relative to a surface of an EUT. When an NDE scanner is moving across the surface of an EUT along two axes of a plane, defined as the X-Y axes, it is desirable to constrain the NDE scanner probe to follow the surface and remain in contact with the surface such that a central axis of the probe will remain transverse or perpendicular to the surface. To accomplish this the NDE scanner probe is usually mounted to a shoe, generally similar to a skid plate, which will slide along the surface of an EUT. The NDE scanner probe shoe usually has forward edges and trailing edges which are arcuately shaped edges to allow the shoe to lift as obstructions are encountered. Various mechanisms and mechanical linkages have been used to allow a shoe to lift along a Z-axis as the probe moves along one or more of the X-Y axes. Several such mechanism are disclosed in U.S. Pat. No. 10,072,745, issued Sep. 11, 2018, having application Ser. No. 15/333,181, filed Oct. 24, 2016, and invented by Harvey Alan Dorsey, which is hereby incorporated by reference as if fully set forth herein It is also desirable that an NDE scanner be deployed by means of aerial drones. However, aerial drones do not provide sufficiently stable platforms during flight for use with the various types of sensor probes noted above for NDE scanners. Aerial drones are able to reach locations relative to EUTs which are difficult for a person to access manually.

SUMMARY OF THE INVENTION

A novel aerial drone deployed NDE scanner is disclosed having a forwardly extending deployment arm through which a cable passes. A winch is mounted to the aerial drone and powered by an electric motor. The cable is wound on the winch and has a terminal end which is secured to the NDE scanner. The NDE scanner is initially mounted to the aerial drone on the end of the deployment arm and held in place by the cable. The NDE scanner is then flown to an initial location on the EUT for inspection. The NDE scanner is then placed on the EUT and magnetically engages against a surface of the EUT, and a section of the cable is spooled from the winch which releases the NDE scanner from the end of the deployment arm. This allows the aerial drone and the NDE scanner to be operated relatively independently, without movement of the drone affecting the orientation of the NDE scanner relative to the EUT and the NDE scanner to be moved independently of the aerial drone. Preferably, an umbilical connection extends between the aerial drone and the NDE scanner, through which power, data and couplant materials may pass between the aerial drone and the NDE scanner. The NDE scanner is later retrieved by reeling the section of cable onto the winch until the deployment arm engages against the NDE scanner, and the NDE scanner may then be removed from the EUT by the aerial drone.

Preferably a smaller, light weight NDE scanner is provided for deployment and retrieval by means of the drone than those typically provided for climbing along an EUT. An NDE scanner is disclosed having a powered cart with two magnetic wheels, one or more drive motors for powering the wheels to turn, and a power supply means to operate the drive motors. The powered cart has a stand-off mechanism which is selectively operated to engage the magnetic wheels of the powered cart with the surface of the EUT, coupling the magnetic wheels to the EUT. The stand-off mechanism is also selectively operated to displace the magnetic wheels from engaging against the surface of the EUT, allowing the powered cart of the NDE scanner to be more easily removed from the surface of the EUT.

The scanner has a sensor probe mounted to a yoke by four sets of two spaced apart offset pins, with one set extending between the sensor probe and the yoke on each four sides of the sensor probe. Each set of the spaced apart offset pins are mounted with spacings between the offset pin pairs being more closely spaced at the lower elevation of the pins than at the upper elevations of the pins. The four sets of two spaced apart offset pins provide for constrained rotation about an X-axis and a Y-axis, when traveling in the X-axis direction or the Y-axis direction, and prevent tipping of a sensor probe. The offset pins are preferably configured such that the center of rotation for the probe is at the bottom of the probe. The sensor probe is pivotally mounted such that it is free to rotate in an angular direction about an X-axis, which is transverse to a direction of travel, and about a Y-axis, which is along the direction of travel. Movement of the sensor probe is constrained to travel in an arc at a constant distance from an axis of the wheels, which contain positional sensors.

DESCRIPTION OF THE DRAWINGS

For a more complete understanding of the present invention and the advantages thereof, reference is now made to the following description taken in conjunction with the accompanying Drawings in which FIGS. 1 through 28 show various aspects for an aerial drone deployed test unit as set forth below:

FIG. 1 is a front, elevation view of an aerial drone deployed test unit which includes an aerial drone and an NDE scanner, showing the NDE scanner after deployment and during use to scan a surface of an EUT;

FIG. 2 is a perspective view of the aerial drone;

FIG. 3 is a perspective view of a test unit attachment mounted to the aerial drone shown in FIG. 2, adapting the aerial drone for use in deploying the NDE scanner;

FIG. 4 is a perspective view of an inward side of the NDE scanner;

FIG. 5 is a perspective view of an outward side of the NDE scanner;

FIG. 6 is a second perspective view of an outward side of the NDE scanner;

FIG. 7 is a partially exploded view of a scanner cart of the NDE scanner;

FIG. 8 is a partially exploded view of a stand-off mechanism and a counter force assembly of the NDE scanner cart;

FIG. 9 is a side elevation view of the scanner cart shown in a deployed position, with the wheels of the scanner cart and the counter force assembly engaging the surface of the EUT;

FIG. 10 is an end view of the scanner cart of FIG. 9, shown in a deployed position, with the wheels of the scanner cart and the counter force assembly engaging the surface of the EUT;

FIG. 11 is a side elevation view of the scanner cart shown in a retrieval ready position, with the standoff member deployed to lift wheels of the scanner cart and the counter force assembly raised from engaging the surface of the EUT;

FIG. 12 is an end view of the scanner cart of FIG. 11, shown in a retrieval ready position, with the standoff member deployed to lift wheels of the scanner cart and the counter force assembly raised from engaging the surface of the EUT;

FIG. 13 is an enlarged portion of the end view of the scanner cart of FIG. 12, showing the standoff member after being deployed to extending beyond the wheels of the scanner cart;

FIG. 14 is a perspective view of a probe assembly for the NDE scanner;

FIG. 15 is an exploded view of the probe assembly for the NDE scanner;

FIG. 16 is a perspective view of a first type of the offset pins which are preferably L-shaped;

FIG. 17 is a perspective view of a second type of the offset pins which are also preferably L-shaped;

FIG. 18 is a perspective view showing the configuration in which the first and second types of offset pins are mounted together to provide a dual gimbal configuration for constrained movement around two axes;

FIG. 19 is a first side elevation view of a shoe of the probe assembly mounted to a yoke, supported from the yoke in a cantilever arrangement by a mated pair of the offset pins;

FIG. 20 is a second side elevation view of the shoe, the yoke and the offset pins, showing the offset pins constraining rotation of the shoe in a first direction;

FIG. 21 is a third side elevation view of the shoe, the yoke and the offset pins, showing the offset pins constraining rotation of the shoe in a second direction;

FIG. 22 illustrates a path that a rotational axis of the shoe travels during the movement shown in FIGS. 19, 20 and 21, constrained by the mated pair of offset pins;

FIG. 23 is a side elevation view showing embodiment in which the configuration of mated offset pins are changed such that the shoe is constrained to rotate along a path located further away from the offset pins than the end of the shoe;

FIG. 24 is a side view of an alternative NDE scanner having a motor and cam mounted to the scanner cart for actuating the engagement member, or push plate, showing the cam and push plate in released positions;

FIG. 25 is a second side view of the alternative NDE scanner having a motor and cam mounted to the scanner cart for actuating the engagement member, or push plate, showing the cam and push plate in actuated positions;

FIG. 26 is an end view of the alternative NDE scanner having a motor and cam mounted to the scanner cart for actuating the engagement member, or push plate, showing the counter force assembly in a lifted position after the cam and push plate are disposed in actuated positions;

FIG. 27 is a partially exploded view of an alternative embodiment to the NDE scanner showing features of an alternative stand-off mechanism for selectively deploying and selectively retrieving the NDE scanner relative to the EUT;

FIG. 28 is a side-elevation view of the alternative embodiment to the NDE scanner during deployment and retrieval, showing the alternative stand-off mechanism in an extended position to lift the wheels of the NDE scanner from the EUT;

FIG. 29 is a side-elevation view of the alternative embodiment to the NDE scanner during deployment and retrieval, showing the alternative stand-off mechanism in an intermediate position with both the stand-off mechanism and the wheels of the NDE scanner contacting the EUT; and FIG. 30 is a side-elevation view of the alternative embodiment to the NDE scanner during deployment and retrieval, showing the alternative stand-off mechanism in a retracted position with the wheels of the NDE scanner fully engaging the EUT and the stand-off mechanism retracted into a housing of the NDE scanner.

DETAILED DESCRIPTION OF THE INVENTION

Figure 1:
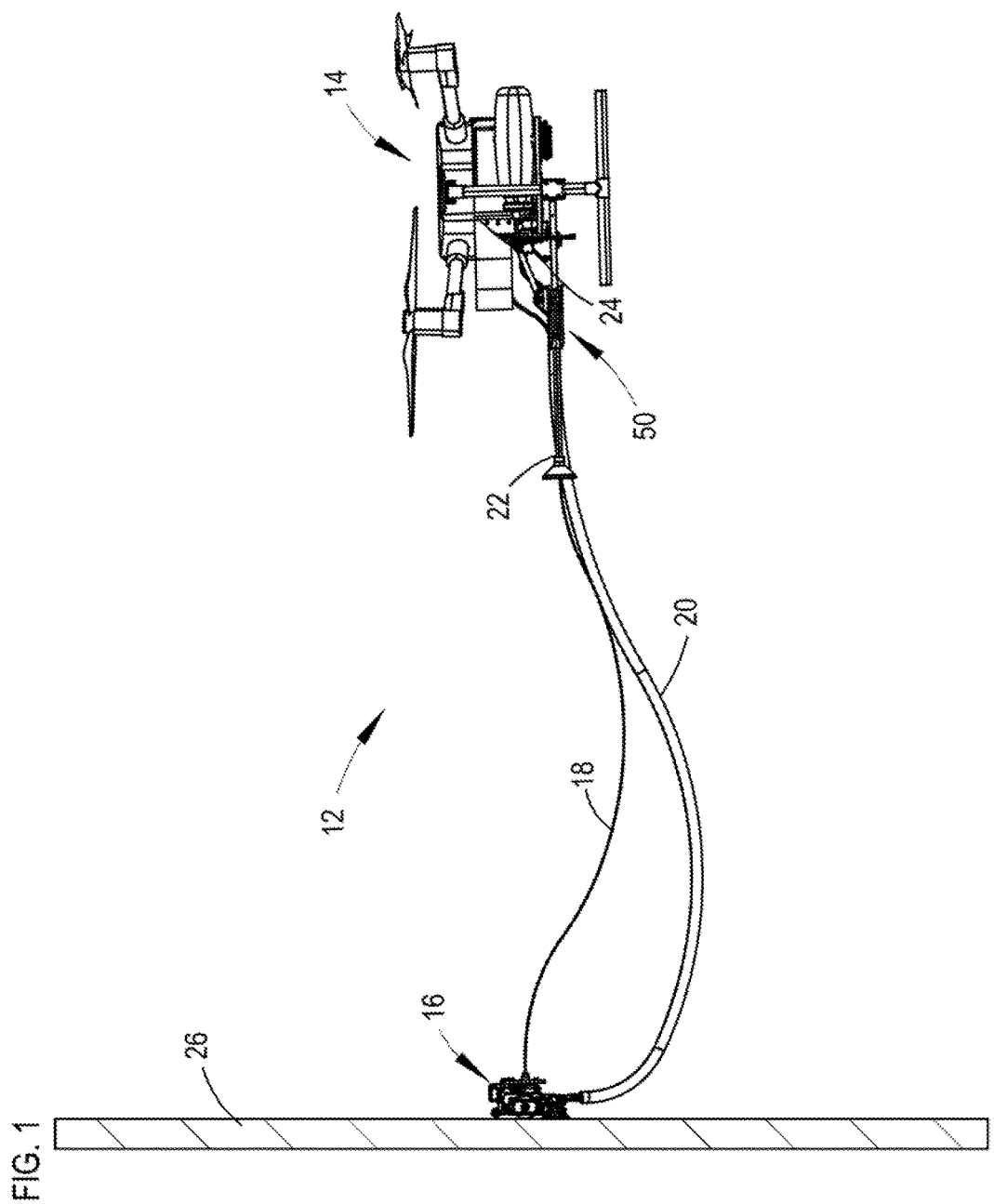

FIG. 1 is a front, elevation view of an aerial drone deployed test unit 12, showing an NDE scanner 16 after deployment from the drone 14 to scan an EUT 26. The test unit 12 includes both a commercially available aerial drone 14 and an NDE scanner 16. The aerial drone 14 has been modified for use by mounting a test unit attachment 50 thereto. The test unit attachment 50 is connected to the NDE scanner 16 by a deployment line 18 and an umbilical connector 20. A deployment arm 22 extends forward from the test unit attachment 50, with a terminal end which is spaced apart from the aerial drone 14. The deployment line 18 is preferably a cable which is selectively dispensed from and spooled onto a winch 24 mounted to test unit attachment 50 affixed to the aerial drone 14. The deployment line 18 is spooled from the winch 24 after the NDE scanner 16 is positioned on the EUT 26, allowing the aerial drone 14 and the NDE scanner 16 to move independent of one another. The NDE scanner 16 is retrieved by the aerial drone 14 approaching the NDE scanner 16 as the line 18 is spooled onto the winch 42. In some embodiments a second winch may be added for spooling the umbilical connector 20. In the present embodiment a second winch is not used, but instead the umbilical connector 20 will remain slack during use.

Figure 2:
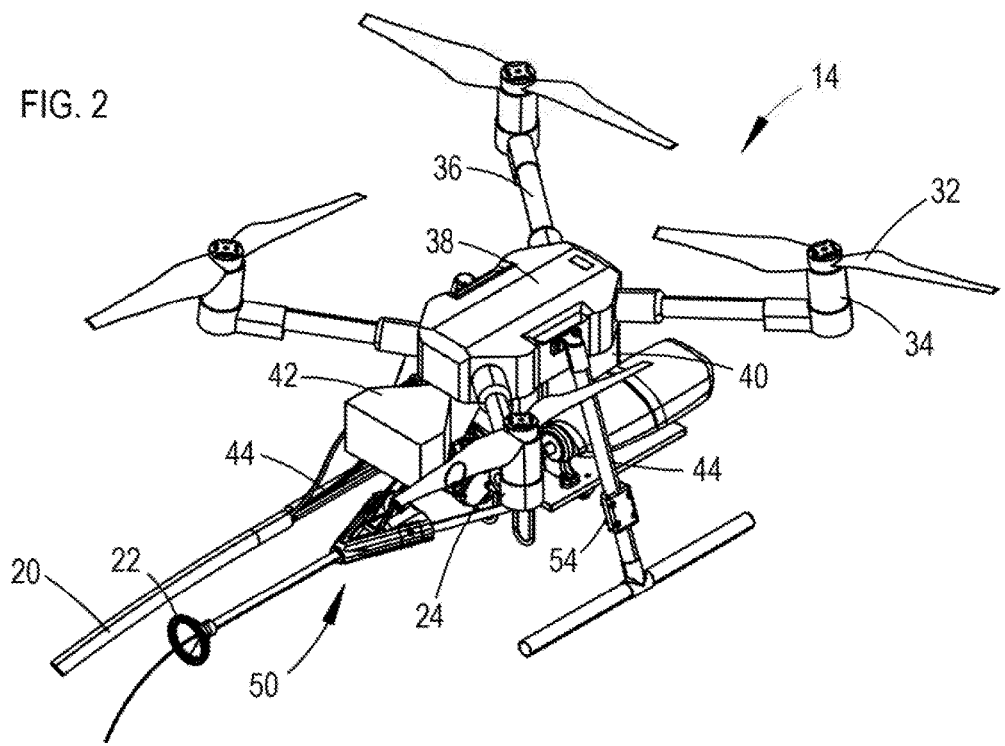

FIG. 2 is a perspective view of the aerial drone 14 with the test unit attachment 50 mounted to the drone 14. The aerial drone 14 is preferably a commercially available drone, such as a Matrice 200 Series drone available from SZ DJI Technology Co., Ltd. of Shenzhen, China. The aerial drone 14 has rotors 32 coupled to respective motors 34, which are mounted to the terminal ends of frame arms 36. A control section 38 is provided for housing control electronics for the drone 14. Batteries 40 are mounted underneath the control section 38. A vision system 42 is mounted to a forward end of the control section 38 and the batteries 40. Landing gear 44 extends downward from the control section 38 and provides a frame for mounting the test unit attachment 50 to the aerial drone 14.

Figure 3:
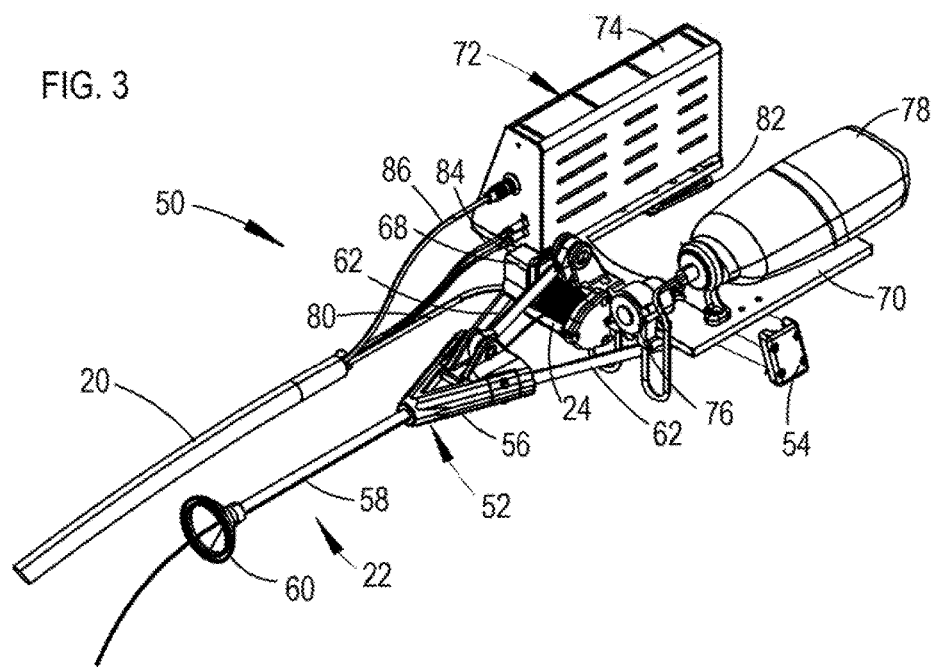

FIG. 3 is a perspective view of a test unit attachment 50 mounted to the aerial drone 14 shown in FIG. 2, for adapting the aerial drone 14 for use in deploying and retrieving the NDE scanner 16. The test unit attachment 50 has a frame 52 which is secured to the landing gear 44 by two frame mounting brackets 54 (one shown). A connector fitting 56 is provided for coupling the deployment arm 22 to the frame 52 and feeding the deployment line 18 through the line guide 60, the extension tube 58 and the connector fitting 56 to the winch 24. The deployment arm 22 is provided by the extension tube 58 with the line guide 60 which are mounted to the forward terminal end of the extension tube 58. The line guide 60 is bell shaped, preferably frusto-conical shaped, for aiding in directing the deployment line 18 into the extension tube 58 without having sharp bends in the line 18. The line guide 60 is also sized to provide a surface of significant size to fit square against the plate 116 which provides the top of the scanner cart 88, with the deployment line 18 pulling scanner cart 88 firmly against the outer rim of the conical-shaped line guide. Connector tubes 62 are part of the frame 52 and extend from the connector fitting 56 to respective ones of the two frame mounting brackets 54 (one shown). The deployment line 18 feeds through the line guide 60, the extension tube 58 and the connector fitting 56 to the winch 24. The deployment line 18 is preferably enclosed within the extension tube 58 and the connector fitting 56. A winch motor 68 is provided for powering the winch 24.

The test attachment unit 50 further includes a mounting plate 70, which is preferably U-shaped for fitting around a forward end of the aerial drone 14. A control panel 72 is mounted on one side of the mounting plate 70 for housing control electronics and providing data storage for the NDE scanner. The control panel 72 may be wirelessly coupled to the NDE scanner by means of radio signals, by means of conventional data signal lines extending through the umbilical 20, or a combination of both. Vents 74 are provided on the control panel 72 for cooling. When an ultrasonic probe is used with the NDE scanner 16, a couplant pump 76 may be located on the mounting plate 70 for pumping ultrasonic couplant fluids to the NDE scanner 16 from a couplant reservoir 78 mounted to the test unit attachment 50. The sonic couplant fluid passes from the reservoir 78, through the couplant pump 76 and through the couplant tubing 80, which passes through the umbilical 20 to the probe assembly 102 shown in FIG. 5. A probe data and power cable 84 passes from the control panel 72, through the umbilical 20 and to the probe assembly 102 shown in FIG. 5. A wireless communication module 82 is mounted to the underside of the mounting plate 70, beneath the control panel 72, and transmits data to a remote computer. A cart data cable 86 passes from the control panel 72, through the umbilical 20 and to the scanner cart 88 shown in FIG. 5. In other embodiments, the cable 86 may also provide power to the scanner cart 88.

FIGS. 4 through 6 are perspective views of the NDE scanner 16 taken from three different directions. FIG. 4 is a view of an inward side of the NDE scanner 16. FIGS. 5 and 6 are views of two different outward sides of the NDE scanner 16. The NDE scanner 16 includes a powered scanner cart 88 having a cart housing 90 and wheels 94, with the wheels 94 extending through the cart housing 90 in rectangular-shaped apertures 92. The wheels 94 are magnetic for operating the powered scanner cart 88 on vertical metal surfaces of the EUT 26. Drive motors 96, preferably provided by closed-loop DC servo motors, are connected to respective ones of the wheels 94, such that the cart 88 is steerable by selectively controlling the angular direction and speed of the motors 96 and the respective wheels 94. Position sensors are preferably integrated into the drive motors 96, and provide outputs to the scanner cart 88 and the control panel 72. A battery holder 98 is mounted to one side of the cart housing 90, and a battery 100 is secured in the battery holder 98. In some embodiments, power may instead be provided through the umbilical connector 20 rather than having a battery holder 98 and battery 100 mounted to the cart 88. A probe assembly 102 is mounted to one side of the cart housing 90 for positioning a sensor probe 232 relative to the EUT 26. A counter force assembly 106 is disposed on an opposite side of the housing 90 from the probe assembly 102, to press against the surface of the EUT 26 and provide a counter force to balance the weight of the probe assembly 102. Two lift mechanisms 108 extend on opposite sides of the housing 90 for lifting the counter force assembly 106 during deployment and retrieval of the NDE scanner 16 relative to the surface of the EUT 26. A stand-off mechanism 114 is incorporated into the cart 88 for assisting in deployment onto the surface of the EUT 26 and removal of the powered cart 88 from the EUT 26. A cable coupling 46 extends through a coupling port 48 formed into the push plate 116 and secures the cart 88 to the deployment line 18, which extends to the aerial drone 14. The push plate 116 provides an engagement member for the deployment arm 22 and line guide 60 of the aerial drone 14.

FIG. 7 is a partially exploded view of the scanner cart 88 of the NDE scanner 16. The scanner cart 88 has a cart housing 90. The probe assembly 102 and two connection fittings 104 are mounted to one side of the housing 90. The connection fittings 104 provide a connection for connecting the cable 86 to the scanner cart 88. The cable 86 extends through the umbilical connector 20 to the aerial drone 14, and in some embodiments may provide power to the scanner cart 88 in addition to a data and control connection. In other embodiments, wireless communication may be used for controlling operation of the scanner cart 88 and the cable 86 may be used for providing power. The cart housing 90 includes an interior cavity 130 and two open sides 132 and 134. Two motor and wheel assemblies 136 provide drive packs which are mounted in respective ones of the open sides 132, 134 of the cart housing 90. A recess 138 is provided into the side of the housing 90 for receiving and mounting a mounting bracket 222 for a mounting pin and two torsion bias springs 218 for the counter force assembly 106. The housing 90 has an open top 140 to which a cover 142 provides an enclosure which is secured to the housing 90 in a fixed position. The cover 142 has a mounting aperture 152 to which a cable coupling 46 is mounted for securing to a terminal end of the deployment line 18. The cable coupling 46 extends through the coupling port 48 which is disposed in a central portion of the push plate 116. The cable coupling 46 and the mounting aperture 152 are centrally located in the cover 142 in a position near the axis for the wheels 94. The cover 142 also includes mounting bosses 144 and 146 for receiving pivot pins 148 and 150, respectively. The pivot pins 148 and 150 provide stationary pivot points for an upper end of the lift mechanism 108.

A control section 154 is provided in an upper portion of the interior cavity 130 and houses circuitry 156. The circuitry 156 preferably comprises electronic circuit boards which have one or more microprocessors and related memory for controlling operation of the scanner cart 88, and in some embodiments instrumentation for the measurement probe of the probe assembly 102. The control circuitry 156 also preferably includes data storage for collected test data from the probe assembly 102. In other embodiments, the control circuitry 156 may be provided within the control panel 72 mounted to the aerial drone 14 and electrically connected to the NDE scanner 16 through the umbilical connector 20, rather than being mounted within the control section 154. The control section 154 may also enclose radio signal receivers and transmitters for wirelessly transmitting data to and receiving control signals from the control panel 72 mounted to the aerial drone 14, or directly to a computer located on the ground. Various combinations of wired and wireless communication may be used.

The motor and wheel assemblies 136 are each drive packs which include a respective one of the motors 96, a motor bracket 160, a drive assembly support 162, a wheel support 164, a drive train 166, the drive shaft 168, bearings 170 and the wheel 94. The two motor and wheel assemblies 136 are mounted to the housing such that one of the assemblies extends a respective one of the open sides 132 and 134 of the cart housing 88. The drive assembly supports 162 are brackets which are mounted directly to one of the open sides of the cart housing 88, preferably with threaded fasteners. Each of the two motor brackets 160 are mounted directly to an interior side of a respective one of the drive assembly supports 162. The motors are mounted to the motor brackets 160. The drive trains 166 with associated gears, bearings and mounting shafts are mounted between the supports 162 and the motor brackets 160. A drive shaft 168 extends outward of the support 162 and through a bearing 170. The wheels 94 are mounted to the drive shafts 168 and held in place by the wheel supports 164 which contain outer wheel bearings. The wheel supports 164 are preferably secured to the drive assembly support 162 by threaded fasteners, as shown in FIG. 7. Pivot pin mounting holes 176 and 178 are preferably provided by threaded holes which receive the pivot pins 182 and 184, respectively. The pivot pin 182 provides a stationary pivot point for the L-shaped arm 186 providing a standoff member for the standoff mechanism 114 shown in FIG. 5. The pivot pin 184 provides a stationary pivot point for the counter force assembly 106. Each of the drive assembly supports 162 has an upwardly facing socket 200 for receiving a bias spring 198 for a respective standoff mechanism 114. The bias springs 198 are preferably coil springs which engage an underside of the L-shaped arm 186 of the stand-off members 118 to push the stand-off members 118 in an upward direction, as viewed in FIG. 7. This spring force combines with the torsion springs 218 in the counter force assembly 106.

Figure 8:
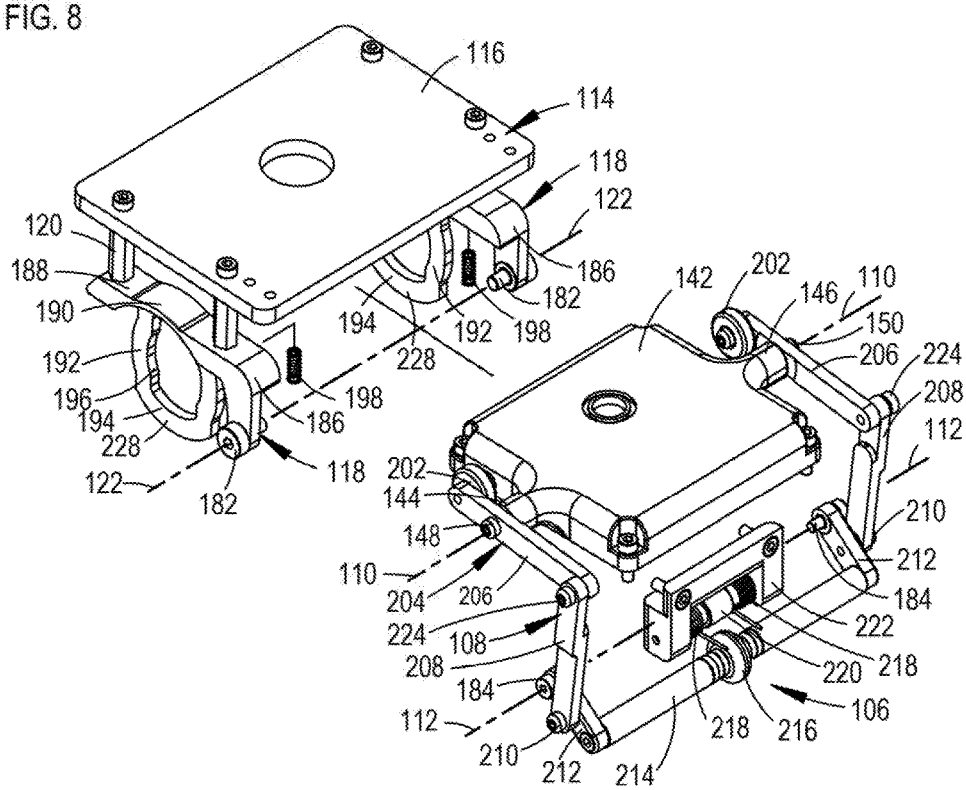
Figure 11:
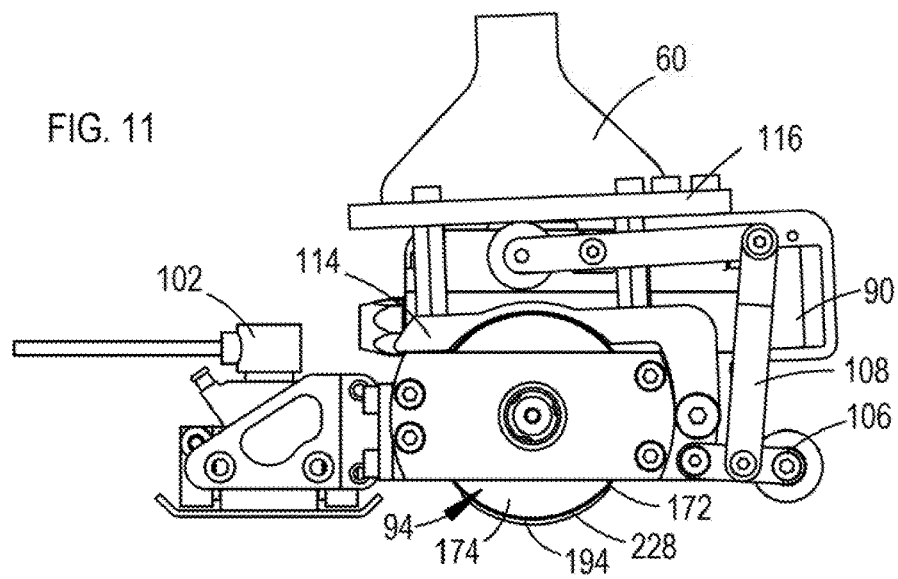
Figure 12:
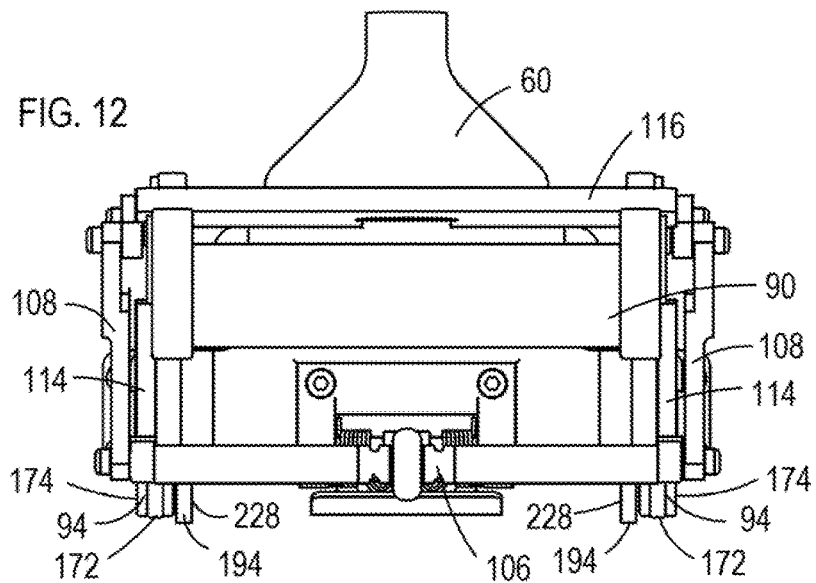
Figure 13:
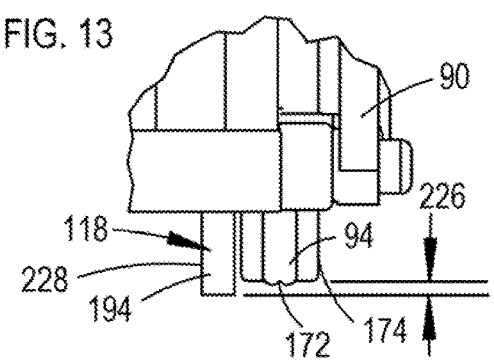

FIG. 8 is a partially exploded view of a stand-off mechanism 114 and a counter force assembly 106 of the scanner cart 88. Referring to FIGS. 7 and 8, the standoff mechanism 114 includes both the standoff members 118 and the push plate 116, which provides an engagement member. The push plate 116 is mounted in fixed relation to the standoff members 118 by fixed couplings 120. The battery holder 98 and the battery 100 are mounted to one side of the push plate 116. The standoff members 118 are preferably provided by L-shaped arms 186. The L-shaped arms 186 have an upper surface 188 which includes an upwardly facing, arcuately shaped section 190, and a planer section 192. The planer section 192 is provided by a plate which extends downward from an underside of the L-shaped arm 186 (as viewed in FIGS. 7 and 8), opposite the upper surface 188. The lower end of the planar section 192 defines a standoff foot 194 and has a side profile 228 which is preferably shaped to be the same as a side profile 174 of one of the wheels 94, but larger to extend forward, rearward and beneath of the side profile of the wheel 94 when the standoff member 118 is moved to an extended position, as shown in FIGS. 11-13, discussed below. A hole 196 extends through a central portion of the planar section 192 for passing the drive shaft 168 and wheel bearings 170, with clearance through the planar section 192 as it is rotated about the axis 122-122.

The entire assembly of the standoff members 118 and the push plate 116 are secured to the cart housing 90 by the threaded fasteners 182, which are threadingly secured to the drive assembly support 162. The standoff members 118 and the push plate 116 will rotate about the axis 122-122 which extends through the central longitudinal axes of the threaded fasteners 182. The bias spring 198 in the socket 200 formed into the top of the drive assembly support 162 will push upwards to urge the standoff members 118 and the push plate 116 to rotate in a clockwise direction as viewed in FIG. 8. Preferably, the line guide 60 of the deployment arm 22 mounted to the aerial drone 14 will press against the push plate 116 while the deployment line cable 18 pulls on the scanner cart housing 90 to pivot the push plate 116 and the standoff members 118 in a counter-clockwise direction as viewed in FIG. 8, when the deployment line 18 is spooled onto the winch 24. Rotating the L-shaped arm 186 of the standoff member 118 in the counter-clockwise direction, as viewed in FIG. 8, will cause the standoff feet 194 of the L-shaped arms 186 to extend beneath the wheels 94, breaking magnetic contact between the wheels 94 and the surface of the EUT 26 being scanned.

The counter force assembly 106 is coupled to the cart housing 90 by pivot pins 184 which are preferably provided by a threaded fastener which secures in the mounting hole 178 in the drive assembly support 162, which itself is secured directly to the housing 90. The counter force assembly 106 will rotate about an axis 112-112 which extends through the central longitudinal axes of the two pivot pins 184. The counter force assembly 106 includes two linkages 212, a bar 214 which extends between corresponding ends of the two linkages 212, and a roller 216. A pin 220 is mounted to the mounting bracket 222 which is secured in the recess 138 in the cart housing 90. Two bias springs 218 are mounted to pin 220 of the mounting bracket 222. The two bias springs are preferably provided by torsion springs which have end arms connecting between the mounting bracket 222 and the bar 214 to urge the roller 216 and the bar 214 into a downward position, or a position extending toward the surface of the EUT 26. The counter force assembly 106 is mounted to the cart housing 90 on a side which is opposite that to which the probe assembly 102 is mounted, for purposes of counter-balancing the weight of the probe assembly 102 and to press the probe assembly 102 into the surface of the EUT 26 which is under test.

When placing the scanner cart 88 on the surface of the EUT 26 and during retrieval of the scanner cart 88 from the surface of the EUT, the counter force assembly 106 pressing downward can interfere with placement of the cart 88. The lift mechanism 108 is provided to overcome these difficulties by actuating to rotate the counter force assembly 106 in a counter-clockwise direction as viewed in FIGS. 7 and 9, which lifts the bar 214 and roller 216 off the surface of the EUT 26. The lift mechanism 108 is provided by two linkages 204, each having a link 206 and a link 208 secured together by a pivot pin 224. The opposite ends of the links 208 from the ends secured to the links 206 are secured to intermediate portions of the links 212 by pivot pins 210, such that movement of the links 208 upward will lift the bar 214 and the roller 216 of the counter force assembly 106. Intermediate portions of the links 206 are secured to the enclosure cover 142 by the pivot pins 148 and 150, which provide stationary pivot points secured in fixed relation to the cover 142 and the cart housing 90. Followers 202 are mounted to the terminal ends of the links 206, which are opposite the ends of the links 206 which are secured to the links 208. The followers 202 are preferably provided by wheels or rollers which are pivotally mounted to the terminals ends of the links 206. The linkages 204 are mounted to the cart housing 90 such that the followers 202 are disposed above the arcuately shaped sections 190 of the upper surfaces 188 of the L-shaped arms 186 of the standoff members 118. When the push plate 116 is pushed downward, the bottom of the push plate 116 will engage the followers 202 causing the links 206 to rotate counter-clockwise about the axis 110-110, as viewed in FIGS. 7 and 8, lifting the links 208 upward and rotating the link 212 counter-clockwise, as viewed in FIGS. 7 and 8, and lifting the counter force assembly 106 away from the surface of the EUT 26.

Figure 9:
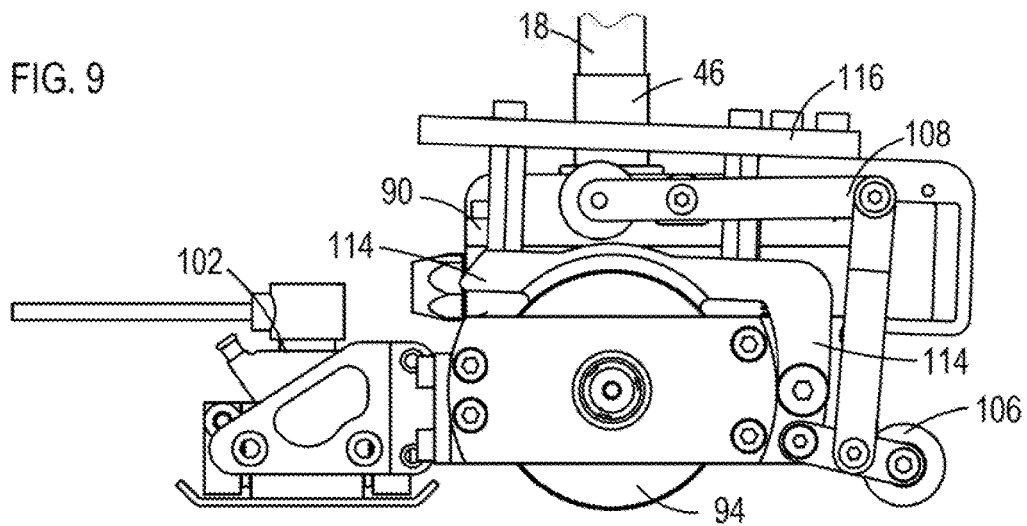
Figure 10:
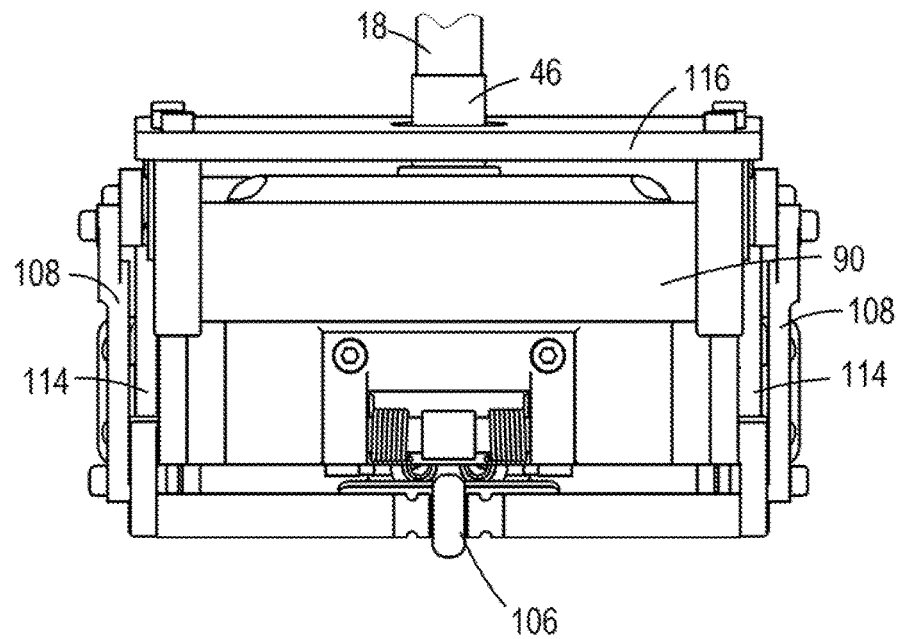

FIG. 9 is a side elevation view and FIG. 10 is an end view of the NDE scanner 16 shown in a deployed position, with the wheels 94 of the scanner cart 88, the counter force assembly 106 and the probe assembly 102 engaging against the surface of the EUT 26 being scanned.

FIG. 11 is a side elevation view and FIG. 12 is an end view of the NDE scanner 16 shown in a retrieval ready position, with the standoff member 118 deployed to lift wheels 94 of the scanner cart 88 and the counter force assembly 106 raised from engaging the surface of the EUT 26. The wheel 94 has a periphery which includes a circumference 172 and a side profile 174. As noted above in reference to FIG. 8, the standoff foot 194 of the arm 186 of the standoff member 118 has a side profile 228 which is preferably shaped to be of similar shape, or the same shape of the wheel 94, with the profile 228 being larger to extend forward, rearward and beneath of the circumference 172 of the wheel 94 when the standoff member 118 is moved to the extended position as shown in FIGS. 11-13. The standoff member 118 extends around and beyond the periphery of the wheel 94, by extending for a larger size than the circumference 172 of the wheel 94.

Figure 14:
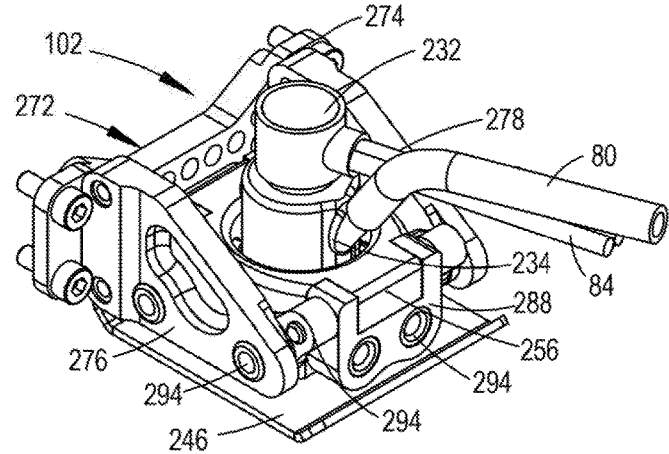

FIG. 13 is an enlarged portion of the end view of the NDE scanner 16 of FIG. 12, showing the standoff member 118 after being deployed, such that the standoff foot 194 is extending beneath the wheel 94, as shown in FIGS. 12 and 13, beyond the circumference of the wheel, lifting the magnetic wheel 94 to separate from the surface of the EUT 26 by a standoff 226. The standoff 226 provides separation distance between the magnetic wheel 94 and the iron in the surface of the EUT 26 to substantially reduce the magnetic force of attraction there-between, requiring less force from the aerial drone 14 to remove the scanner cart 88 from the EUT 26. The side profile 228 of the standoff foot 194 extends beneath the side profile 172 of the wheel 94, that is, beyond the circumference 174 of the wheel, by a distance of the standoff 226, FIG. 14 is a perspective view and FIG. 15 is an exploded view of the probe assembly 102 used for the NDE scanner 16. Coordinate axes are shown in FIG. 15, defining an X-axis, a Y-axis and a Z-axis which as used herein are defined relative to the scanner cart 88. The scanner cart will move in a direction parallel to the Y-axis when moving in a forward direction. The probe assembly 102 has the sensor probe 232 which is secured within a first mounting member 234. The first mounting member 234 is preferably in the general form of a sleeve having a body 236 which is generally cylindrical. Two mounting bosses 238 are provided on opposite sides of the body 236, each having pin ports 240 for receiving the longitudinal pins 290. A coupling fluid tube connector 242, shown in FIG. 15, extends from one side of the first mounting member 234 for connecting to the fluid tube 80, shown in FIG. 14. Three permanent magnets 244 are located in the inward side of the mounting member 234 for assisting in pulling the sensor probe 232 in close proximity to the surface of the EUT 26. A shoe 246 is secured to the inward end of the mounting member 234 by two threaded fasteners 250 which extend through two holes 248 in the shoe 246. An aperture 252 extends through a central portion of the shoe 246 for passing a lower end of the scanner probe 232. A set screw 254 is provided for securing the scanner probe 232 to the body 236 of the first mounting member 234. A second mounting member 256 preferably is provided by a ring having an annular-shaped body 258. A central aperture 260 extends through the center of the body 122 for loosely fitting around the first mounting member 234. Two mounting bosses 266 extend from opposite sides of the second mounting member 256 and have mounting pin ports 268 extending there-through for receiving two transverse pins 292.

A yoke 272 is provided by a back plate 274, a first arm 276 and a second arm 278. The first arm 276 and the second arm 278 extend in parallel, orthogonal to the back plate 274. A first bracket 280 and a second bracket 282 extend in parallel, and parallel to the back plate 274. Pin ports 284 extend through the first and second brackets 280 and 282, adjacent to respective channels 286 formed into the first and second brackets 280 and 282. Two longitudinal pins 290 extend in parallel, through respective ones of the pin ports 240 in mounting bosses 238. Two transverse pins 292 extend in parallel through respective ones of the pin ports 268 and 284, the mounting bosses 266 of the second mounting member 256, and the first and second brackets 280 and 282. Four sets of two offset pins 294 and 354 are provided for securing the first and second mounting members 234 and 256 to the yoke 272. Mounting pins 304 and threaded fasteners 306 are provided to secure the first arm 276 and the second arm 278 to the back plate 274.

Two sets of the offset pins 294 have first sections 296 which include apertures 302 which are configured for rotatably receiving respective terminal ends of the transverse pins 292, and second sections 298 which are rotatably received in the offset pin ports 288 of the first arm 276 and the second arm 278 of the yoke 272. The yoke 272 and the offset pins 294 are configured to secure the second mounting member 256 to the yoke 272, constrained to rotate about the X-axis. The second mounting member 256 is preferable annular-shaped. Two pairs of the offset pins 354 have first sections 356 which are configured for rotatably receiving respective terminal ends of the longitudinal pins 290, and second sections 358 which are rotatably received in the offset pin ports 288 of respective ones of the first and second mounting members 280 and 282. The second mounting member 256 and the mounting brackets 280 and 282 are configured to secure the first mounting member 234 to the second mounting member 256, constrained to rotate about the Y-axis.

This configuration provides a double gimbal arrangement with the mated pairs of the offset pins 294 restricting movement of the shoe 146 and the sensor probe 232 in around the X-axis, and the mated pairs of the offset pins 354 restricting movement of the shoe 146 and the sensor probe 232 in around the Y-axis. The restricted movement of the sensor probe 232 and the shoe 246 along the X axis and the Y axis provides substantially parallel orientation of the terminal end of the sensor probe 232 and the shoe 246 to the surface of the EUT 26.

FIG. 16 is a perspective view of the offset pin 294, which is preferably L-shaped when viewed from a side elevation view. The offset pin 294 each has a first section 296, a second section 298 and an offset section 300 extending between the first section 296 and the second section 298. The first section 296 preferably has an aperture 302 which extends for rotatably receiving one of the transverse pins 292, which defines an axis of rotation 310. The second sections 296 preferably have bearing surfaces which are rotatably received within an aperture defining an offset pin port 288 in the yoke 272 (or the second mounting member 256) from which the respective offset pin 294 is suspended, defining an axis of rotation 312. The distances between the axis 310 and 312 define a offset length 314.

FIG. 17 is a perspective view of the offset pin 354, which is similar in shape to the offset pin 294 when viewed from a side elevation view, but in this particular embodiment the offset pin 354 has a shorter overall length than the offset pin 294. The offset pin 354 has a first section 356, a second section 358 and an offset section 360 extending between the first section 356 and the second section 358. The first section 356 preferably has an aperture 362 which extends for rotatably receiving one of the longitudinal pins 290, which defines an axis of rotation 370. The second section 358 preferably has a bearing surface which is rotatably received within one of the offset pin ports 288, which are located in one of the first bracket 280 and the second bracket 282. Rotation of the second section in a respective pin port will define an axis of rotation 372. The distance between the axes 370 and 372 defines an offset length 374.

FIG. 18 is a perspective view showing the configuration in which the first offset pins 294 and the second offset pins 354 are mounted together to provide a dual gimbal configuration for constrained movement about two axes, the X-axis and the Y-axis. The mated pairs of offset pins 294 and 354 are preferably configured in an alignment such that the ends of the offset pins 294 and 354 closest to the surface of the EUT 26 are closer together than the ends which are located further from the EUT surface. That is, for the offset pins 294 the second sections 298 and the axes 312 are spaced closer together than the first sections 296 and the axes 310. For the offset pins 354 the second sections 358 and the axes 362 are spaced closer together than the first sections 356 and the axes 370. When the NDE scanner 16 is operated on a horizontal surface of the EUT 26, the lower ends of the respective two pairs of offset pins 294 are located closer together than the upper ends of the offset pins 294, and the lower ends of the two pairs of offset pins 354 are located closer together than the upper ends of the offset pins 354. Referring to one set of the offset pins 294, projection lines 316 (shown in FIG. 19) extend through the axes of rotation 310 and 312 for the mated two of the offset pins 294 and will intersect to define a central axis of rotation 318 about either the Y-axis or the X-axis, depending upon the orientation of the particular offset pins 294. The shoe 246 will rotate about the central axis of rotation 318 when a disturbance is encountered by the shoe 246 moving along the surface of the EUT 26.

FIG. 19 is a side elevation view of the second mounting member 256, the probe 232, and the two offset pins 294 which are connected there-between and working as a mated pair. The following discussion is applicable to the mated pairs of the offset pins 354, but parameters for only one pair of the offset pins 294 are discussed below. The mated pair of the offset pins 294 extending between the yoke 272 and the second mounting member 256 will perform in similar manner as described in the following, except that the lengths 346 may be selected to be of a different length than that of the offset pins 294 connecting between the second mounting member 256 and the probe 232. The offset pins 294 shown in FIG. 19 will rotate about the X-axis, and will constrain rotation of the probe 232 relative to the second mounting member 256. As noted above, the pivotal connections for the mated pairs of the offset pins 294 located closest to the shoe 246 are spaced closer together than the pivotal connections for the offset pins 294 located further away from the shoe 246, and the surface of the EUT 26. The offset length 314 and the spacing between the axes 312 relative to the axes 310 of the mated pair of the offset pins 294 will determine the center of rotation 318 for the probe 232 about the X-axis and the accuracy about which the assembly rotates around the focal point or center of rotation 318.

The yoke 272, the second mounting member 256, and the first mounting member 234 to which the probe 232 is fixed, are connected together in a double gimbal arrangement by two sets of pairs of the offset pins 294, with the lengths and spacing for mated pairs of the offset pins 294 constraining rotation of connected members about the X-axis and the Y-axis, respectively. The constraint to movement of the shoe 246 provided by this configuration assists in maintaining the sensor probe 232 in flat, intimate contact with a variable surface while being moved over the surface, providing a gantry mechanism. The two rotational axes 318 of compliance will be degrees of freedom about the two perpendicular lines which are parallel to the X- and Y-axes, and should ideally pass through the vertical centerline at the bottom, terminal end of the probe 232, preferably at the bottom of the shoe 242, which is the end closest to the EUT surface being measured for vertical surfaces. These two degrees of freedom will allow the shoe 246 to maintain flat contact with a surface that may vary from being absolutely parallel to the plane of the probe 232. Preferably, the shoe 246 will be held against the surface of the EUT 26, either by gravity or by spring pressure such as that provided by the counter force contact assembly 106.

Figure 20:
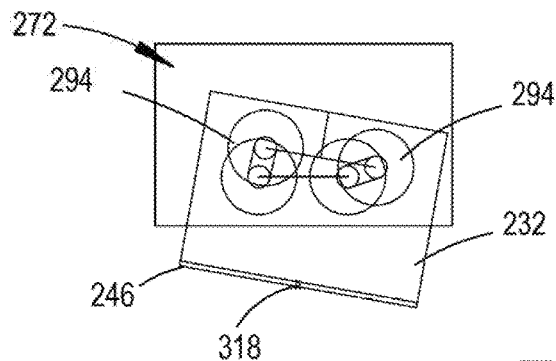
Figure 21:
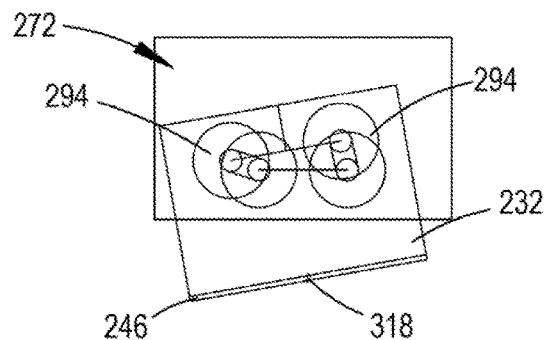
Figure 22:
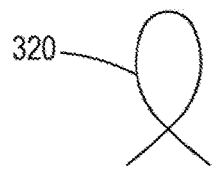

FIGS. 20 and 21 show the shoe 246 rotating as constrained by the mated pair of offset pins 294. The axis 318 about which the end of the shoe 246 nearest to the EUT surface rotates will follow a path 320, shown in FIG. 22. FIG. 22 shows the path 320 that the axis 318 at the end of the shoe 246 closest to the EUT surface follows in rotation constrained by the mated pair of offset pins 294. The path 320 is shown in FIGS. 19, 20 and 21, but is almost imperceptible.

Figure 23:
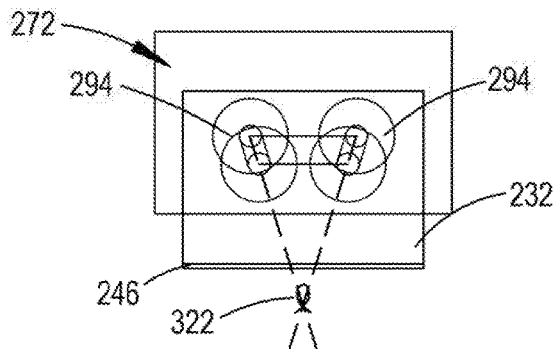

FIG. 22 illustrates a path 320 that the rotational axis 318 of the shoe 246 travels during the movement shown in FIGS. 19, 20 and 21, constrained by the mated pair of offset pins. In FIG. 23 the center of the shoe 246 is spaced apart from the projected vertexes 318 of offset lines 316, further away from the surface of the EUT. With further rotational movements, the path of axis 318 deviates from the pseudo rotational point and moves in the path displayed in FIG. 22. In the arrangement of FIG. 19, the two projection lines 316 passing through the offset dimensions 314 of the offset shafts 294 are configured to converge at the desired point of rotation 318. For very small rotational movements, the shoe 246 rotates substantially about that point 318 with high precision. The mechanics of this arrangement are also substantially conducive to overcoming the tipping moment, and the reaction of the shoe 246 in being pushed away from a point of obstruction or elevated surface protrusion will raise the edge of the shoe 246 at that point. This will assist the shoe 246 in ramping up and over a protrusion. With further rotational movements, the path of the convergence axis 318 deviates from the pseudo rotational point and moves in the path 320 displayed in FIG. 22. As well as providing the desired reluctance to tipping, the error is also reduced over the practical range of the mechanism, which for example for ultrasonic transducer probes, is typically +/−10 degrees. In practice, this is a sufficient range to compensate for differences between a plane defined by the show 246 and a larger plane defined by the center of wheels and the contact point of the show 246. In both FIGS. 20 and 21, the shoe 246 is rotated 8 degrees.

In FIG. 23 the center face of the shoe 246 is configured with projected lines 316 through respective axes 310 and 312 being focused such that the rotation axis 322 of the shoe 246 is located beneath the shoe 246. This configuration may be achieved by lengthening the offset distance 314 between the axes 310 and 312, or by changing the spacings between respective ones of ends 296 and 298, or a combination of both. The path 322 will be larger in FIG. 23 than the path 320 shown in FIGS. 19 through 21, with a lower focal point due to the longer lengths of the pin offsets 314 and the projection lines 316 from that of FIGS. 19 through 21. The modifications to the configuration of the offset pin 294 results in the convergence of the projection lines 316 at a point 322 below the shoe 246, as shown in FIG. 23 at the zero degree rotation point, which results in further restriction of the rotation of the shoe 246 to rotation of less angular displacement than that of the configuration shown in FIGS. 19 through 21.

Figure 24:
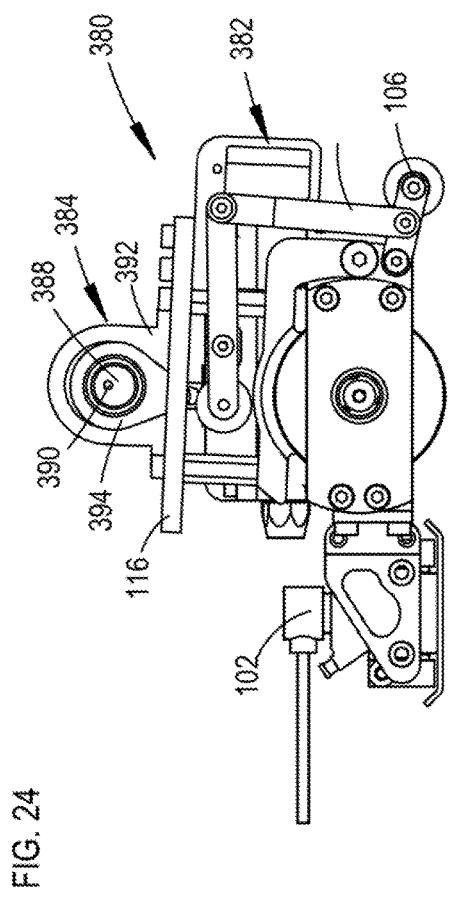

FIG. 24 is a side view of an alternative NDE scanner 380 having actuator 384 mounted to push plate 116, which pull the scanner cart 382 toward the push plate 116. The actuator 384 and the push plate 116 are shown in released positions. The actuator 384 includes a closed-loop DC servo motor 386 and cam 388. The cam 388 is mounted to a rotary shaft 390. The cam 388 is rotatably connected to a link 394, disposed in an aperture in the link 394 with a journal bearing defined there-between. The link is connected to the top of the housing for the scanner cart 382. The actuator 384 is mounted atop the scanner cart 382 by means of a mounting bracket 392, preferably mounted to the plate 116. The wheels 94 and the counter force assembly 106 are shown in released positions.

Figure 25:
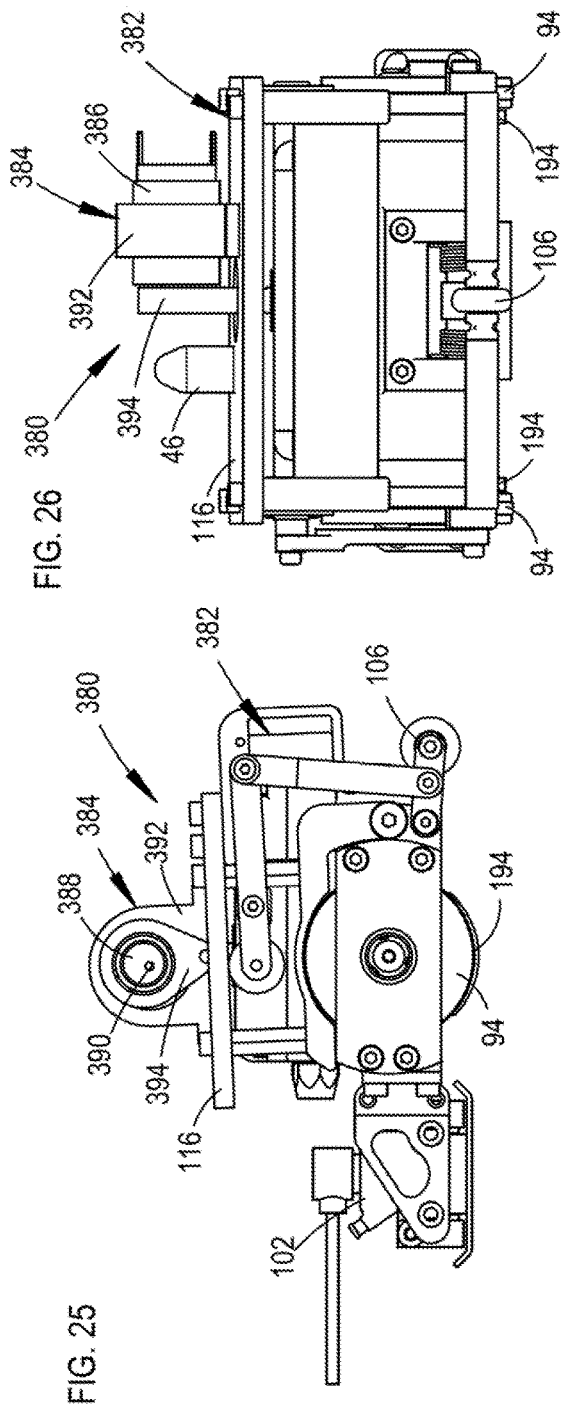

FIG. 25 is a second side view of the alternative NDE scanner 380 showing actuator 384 having operated to power the motor 386 to move the cam 388 into a position in which the scanner cart 382 is pulled toward the push plate 116, moving the standoff foot 194 into an extended position and lifting the counter force assembly 106.

Figure 26:
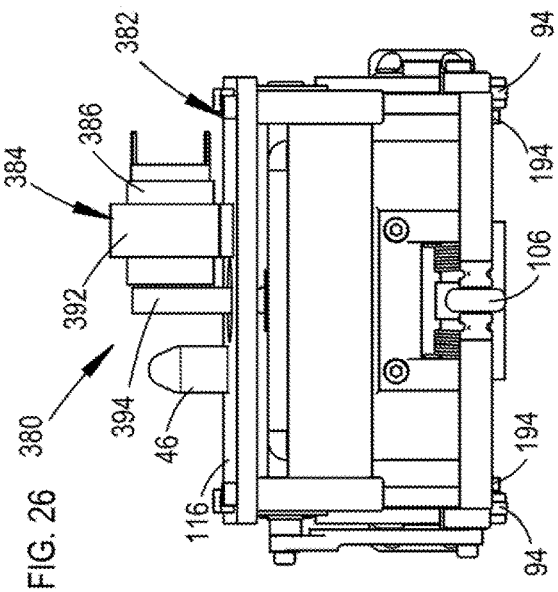

FIG. 26 is an end view of the alternative NDE scanner 380 showing the actuator 384 in an intermediate position, with the standoff foot 194 no longer extended to raise the wheel 94 and the counter force assembly 106 remaining in a lifted position. A coupling 46 is mounted to the plate 116 for coupling to a cable connecting to an areal drone, such as the deployment line cable 18 of FIG. 1. The coupling 46 may also be mounted directly to the housing for the scanner cart 382 with a port for passing through the plate 116, similar to the port 48 shown in FIG. 7. In other embodiments a U-shaped bracket (not shown) may be provided for connecting the scanner cart 382 to a cable connecting to an aerial drone.

FIG. 27 is a partially exploded view of an alternative embodiment NDE scanner 324 showing features of a stand-off mechanism 330 for selectively mounting the NDE scanner 324 to the EUT 26. The stand-off mechanism 330 includes an engagement member 332, which is preferably provided by a plate. Stand-off members 334 are preferably provided by four pins, but in other embodiments one or more pins may be used. The stand-off members 334 have first terminal ends connected to the engagement member 332. One or more bias springs 336 (four shown) extend between the engagement member 332 and an outward side of the cart housing 328 to urge the engagement member 332 to move away from the cart housing 328. The stand-off members 334 extend through the bores 388 to pass through the cart housing 328. The lengths of the stand-off members 334 are configured such that when the engagement member 332 is pressed downward against the force of the bias springs 336, the inward terminal ends 340 of the stand-off members 334 will extend from the inner side of the cart housing 328 for a distance which is further than a pair of spaced apart magnetic wheels 342 extending there-from. This provides separation from the wheels 342 and the surface of the EUT 26 to significantly reduce the magnetic coupling between the wheels 342 and the EUT 26, allowing the aerial drone 14 to more easily retrieve the NDE scanner 324 from the EUT 26. The stand-off mechanism 330 is extended to assist in deployment of the NDE scanner 324 by preventing magnetic coupling between the wheels 342 and the EUT 26 until the aerial drone 14 has placed the NDE scanner 324 in a selected position relative to the EUT 26.

FIGS. 28 through 30 are side-elevation views of the alternative embodiment NDE scanner 324 during deployment and retrieval using the aerial drone 14. FIG. 28 shows the alternative stand-off mechanism 330 in an extended position to lift wheels 342 of the NDE scanner 324 from the EUT 26. FIG. 29 is a side-elevation view of the alternative embodiment to the NDE scanner 324 during deployment and retrieval, showing the stand-off mechanism 330 in an intermediate position with both the alternative stand-off mechanism 330 and the wheels 342 of the NDE scanner 324 contacting the surface of the EUT 26. FIG. 30 is a side-elevation view of the alternative embodiment to the NDE scanner 324 during deployment and retrieval, showing the alternative stand-off mechanism 330 in a retracted position with the wheels 342 of the NDE scanner 324 fully engaging the EUT 26 and the stand-off mechanism 330 fully retracted into the cart housing 338 of the NDE scanner 324.

The present disclosure provides advantages of an NDE scanner which is deployed and retrieved by means of an aerial drone. The NDE scanner is deployed onto an EUT and has magnetic wheels allowing the NDE scanner to move over the EUT, on vertical and other non-horizontal surfaces. The NDE is retrievable by the aerial drone and includes a stand-off mechanism, selectively operable for separating the magnetic wheels from contacting the surface of the EUT to selectively release the NDE scanner from the EUT for retrieval by the aerial drone. The present disclosure further provides a dual gimbal arrangement provided by four sets of offset pins configured to provide constrained rotation about both an X-axis and a Y-axis, and preventing tipping of a probe sensor, while allowing movement of the probe sensor over surface non-conformities.

Although the preferred embodiment has been described in detail, it should be understood that various changes, substitutions and alterations can be made therein without departing from the spirit and scope of the invention as defined by the appended claims.

What is claimed is:

1. An apparatus for aerial deployment of an NDE scanner for inspecting conditions of an EUT, comprising: an aerial drone; an NDE scanner having a powered cart to which an NDE probe is secured, said powered cart being configured for steering over a surface of the EUT; a deployment line extending between said aerial drone and said powered cart, interconnecting there-between configured for deployment and retrieval of said powered cart relative to said aerial drone; a powered winch mounted to said aerial drone, wherein said powered winch is configured for spooling said deployment line from and onto a drum of said winch during deployment and retrieval, respectively, of said powered cart relative to said aerial drone; a deployment arm mounted to said aerial drone, wherein said deployment line is connected to said deployment arm configured for respectively aligning said powered cart and said aerial drone configured for placing said powered cart relative to the EUT during deployment and retrieval of said powered cart from the EUT; and wherein said aerial drone is located relative to the EUT configured to place said powered cart proximate the surface of the EUT, with said deployment line extending between said aerial drone and said powered cart, said aerial drone configured to release said powered cart to operate independently of said aerial drone, and said deployment line configured to be spooled onto said winch to align said deployment arm between said aerial drone and said powered cart.

2. The apparatus according to claim 1, a couplant reservoir and a couplant pump mounted to said test unit attachment configured for supplying a couplant to said NDE probe mounted to said powered cart with a couplant tube extending from said test unit attachment to said powered cart.

3. The apparatus according to claim 2, a couplant reservoir and a couplant pump mounted to said test unit attachment for supplying a couplant to said NDE probe mounted to said powered cart with a couplant tube extending from said test unit attachment to said powered cart.

4. The apparatus according to claim 3, wherein said couplant is a fluid couplant.

5. The apparatus according to claim 3, wherein said deployment line is a different element from said couplant tube.

6. The apparatus according to claim 2, wherein said deployment line is a cable formed of flexible material configured for spooling onto said drum of said powered winch.

7. The apparatus according to claim 2, wherein said deployment line extends through said deployment arm, and a hollow, frusto-conical shaped bell is included on an end of said deployment arm configured to provide a line guide; and said deployment line extends from said powered winch, through said deployment arm and said line guide, to said powered cart.

8. The apparatus according to claim 2, further comprises a control panel mounted to said test unit attachment configured for controlling operation of said aerial drone, said powered winch and said couplant pump; and further comprising a radio signal transmitter mounted to said test unit attachment and coupled with said control panel.

9. The apparatus according to claim 1, wherein said powered cart is a scanner cart, comprising: two wheels having a common axis of rotation, said wheels being formed of magnetic materials which provide a magnetic contact force with a ferro-magnetic material of the EUT; two independent drive motors, one for each of said two wheels, such that said scanner cart is driven in a line along the Y-axis and also steered in directions along an X-axis; and a probe shoe securing said NDE probe to said scanner cart, with said probe shoe disposed a fixed distance from said wheels; said probe shoe mounted to said scanner cart with two rotational axes degrees of freedom about the X-axis and the Y-axis at the contact point at the face of the probe, with the rotation about a single point on the surface having constant location relative to the wheels.

10. The apparatus according to claim 9, further comprising a contact member consisting of a bar and a contact wheel which is pressed against the surface of the EUT by a spring force, to thereby provide a reactive force about the wheel axis resulting in constant contact of the probe shoe to the surface of the EUT; and wherein said bar and said contact wheel are disposed on an opposite side of said scanner cart from said probe shoe.

11. The apparatus according to claim 9, wherein one or more permanent magnets are disposed in said probe shoe configured for pulling said probe shoe into the surface of the EUT.

12. The apparatus according to claim 9, further comprising a stand-off mechanism with one or more standoff members which are disposed aside of respective ones of said two wheels, said standoff members having side profiles which are sized for extending forward, rearward and beneath circumferences of said wheels when said standoff members are disposed in extended positions, wherein said standoff members are selectively moved to said extended positions to lift said wheels off the surface of the EUT to reduce the magnetic contact there-between.

13. The apparatus according to claim 12, wherein said standoff members are moved to said extended positions by selectively applying force to a top of said scanner cart, and said force is transmitted to said standoff members.

14. The apparatus according to claim 13, wherein said force is applied by pushing said deployment arm into said scanner cart with said aerial drone to thereby extend said standoff members forward, rearward and beneath said circumferences of said wheels.

15. The apparatus according to claim 13, wherein said force is applied by an actuator mechanism comprising a cam mounted to a rotary shaft of a motor which applies force to said scanner cart to thereby extend said standoff members forward, rearward and beneath said circumferences of said wheels.

16. The apparatus according to claim 9, further comprising a dual gimbal arrangement which secures said probe shoe to said scanner cart and provides said two rotational axes degrees of freedom about the X-axis and the Y-axis at the contact point at the face of the probe, wherein said dual gimbal arrangement provides anti-tip functionality, and further includes: two sets of four offset pins, each of said two sets of four offset pins arranged for constraining rotation about a respective one of the X-axis and the Y-axis, wherein each of said four offset pins have two pairs of said offset pins which are aligned in a spaced arrangement with distal ends of said two offset pins aligned for rotating about parallel axes, wherein a first two of said parallel axes are closer to said EUT and a second two of said parallel axes are further from said EUT, and said first two of said parallel axes which are closer to said EUT are spaced closer together than said second set of parallel axes which are further from said EUT; and wherein said two sets of four offset pins are disposed in transverse relation, such the respective ones of said parallel axes of said two sets of offset pins are disposed in orthogonal relation, constraining said probe shoe to rotate about said X-axis and said Y-axis.

17. The apparatus according to claim 16, wherein said two sets of four offset pins have each pair of adjacent pins aligned with terminal ends closest to said EUT spaced closer together and terminal ends furthest from said EUT spaced further apart, and lengths of said pair of adjacent pins configured to define respective focal points about which said probe shoe is confined to rotate respective one of said X-axis and said Y-axis, said focal point defined by said spacings between and lengths of said pair of adjacent offset pins.

* * * * *